United States Patent
Hall et al.

(10) Patent No.: US 8,214,021 B2
(45) Date of Patent: Jul. 3, 2012

(54) MEDICAL IMAGING SYSTEM AND METHOD CONTAINING ULTRASOUND DOCKING PORT

(75) Inventors: Anne Lindsay Hall, New Berlin, WI (US); Vincent Stanley Polkus, Delafield, WI (US); Lucas Delaney, Milwaukee, WI (US); Stephen Metz, Kenmore, WA (US)

(73) Assignee: General Electric Company, Schenectady, NY (US)

( * ) Notice: Subject to any disclaimer, the term of this patent is extended or adjusted under 35 U.S.C. 154(b) by 724 days.

(21) Appl. No.: 12/336,288

(22) Filed: Dec. 16, 2008

(65) Prior Publication Data

US 2010/0152583 A1    Jun. 17, 2010

(51) Int. Cl.
*A61B 5/05* (2006.01)
*A61B 8/00* (2006.01)

(52) U.S. Cl. ........................................ 600/427; 600/437

(58) Field of Classification Search .................. 600/427, 600/437, 440; 378/163; 382/132
See application file for complete search history.

(56) References Cited

U.S. PATENT DOCUMENTS

| | | | |
|---|---|---|---|
| 5,437,278 A | 8/1995 | Wilk | |
| 6,447,451 B1 | 9/2002 | Wing et al. | |
| 6,475,146 B1 | 11/2002 | Frelburger et al. | |
| 6,480,565 B1 | 11/2002 | Ning | |
| 6,497,661 B1 | 12/2002 | Brock-Fisher | |
| 6,775,404 B1 | 8/2004 | Pagoulatos et al. | |
| 6,795,571 B2 | 9/2004 | Kusch | |
| 6,980,419 B2 | 12/2005 | Smith et al. | |
| 6,987,831 B2 | 1/2006 | Ning | |
| 7,115,093 B2 | 10/2006 | Halmann et al. | |
| 7,412,027 B2 | 8/2008 | Yakubovsky et al. | |
| 2004/0150963 A1 | 8/2004 | Holmberg et al. | |
| 2004/0236206 A1 | 11/2004 | Sakas et al. | |
| 2005/0049497 A1 | 3/2005 | Krishnan et al. | |
| 2005/0251035 A1 | 11/2005 | Wong et al. | |
| 2005/0288581 A1 | 12/2005 | Kapur et al. | |
| 2006/0030768 A1 | 2/2006 | Ramamurthy et al. | |
| 2006/0034508 A1 | 2/2006 | Zhou et al. | |
| 2006/0116578 A1 | 6/2006 | Grunwald et al. | |
| 2006/0136259 A1 | 6/2006 | Weiner et al. | |
| 2006/0155577 A1 | 7/2006 | Niemeyer | |

(Continued)

FOREIGN PATENT DOCUMENTS

EP        1643444        5/2006

(Continued)

OTHER PUBLICATIONS

Boone et al, Dedicated Breast CT: Radiation Dose and Image Quality Evaluation, Radiology 221:657-667 (2001).

(Continued)

*Primary Examiner* — Michael Rozanski
(74) *Attorney, Agent, or Firm* — The Small Patent Law Group; Dean D. Small

(57) ABSTRACT

An ultrasound medical imaging system and non-ultrasound medical imaging system are combined and communicate via a suitable docking port, which is supported by the non-ultrasound medical imaging system and configured to receive the ultrasound medical imaging system. The systems can communicate directly, indirectly, and/or wirelessly. Each can also be configured for cross-imaging in the other modality, displaying medical imagery from the other modality on respective and/or combined displays, and/or control by a user interface of the other and/or a common user interface. Registry between patient imagery is possible, and improved workflow is provided.

20 Claims, 5 Drawing Sheets

U.S. PATENT DOCUMENTS

| | | |
|---|---|---|
| 2006/0173303 A1 | 8/2006 | Yu et al. |
| 2006/0264749 A1 | 11/2006 | Weiner et al. |
| 2007/0016442 A1 | 1/2007 | Stroup |
| 2007/0168308 A1 | 7/2007 | Wang et al. |
| 2007/0237371 A1 | 10/2007 | Zhu et al. |
| 2007/0263768 A1* | 11/2007 | Ullberg et al. ............... 378/63 |
| 2008/0009724 A1 | 1/2008 | Lee et al. |
| 2008/0218743 A1 | 9/2008 | Stetten et al. |
| 2008/0219540 A1 | 9/2008 | Ter Mors |
| 2010/0063400 A1* | 3/2010 | Hall et al. ............... 600/466 |
| 2010/0152578 A1* | 6/2010 | Hall et al. ............... 600/437 |

FOREIGN PATENT DOCUMENTS

| | | |
|---|---|---|
| WO | W02006111871 | 2/2006 |
| WO | W02006111874 | 2/2006 |
| WO | W02007133143 | 11/2007 |

OTHER PUBLICATIONS

Chen at al, Cone-beam volume CT mammographic imaging: feasibility study, Proc. SPIE vol. 4320: 655-664 (2001).

Pagoulatos, et al., Interactive 3-D Registration of Ultrasound and Magnetic Resonance Images Based on a Magnetic Position Sensor, IEEE Transactions on Information Technology in Biomedicine, vol. 3, No. 4, Dec. 1999, p. 278-288.

* cited by examiner

MEDICAL IMAGING SYSTEM AND METHOD CONTAINING ULTRASOUND DOCKING PORT

CROSS-REFERENCE(S) TO RELATED APPLICATION(S)

—

STATEMENT REGARDING FEDERALLY SPONSORED RESEARCH OR DEVELOPMENT

—

REFERENCE(S) TO MICROFICHE APPENDIX AND/OR COPYRIGHT PROTECTION

—

BACKGROUND

1. Field of Invention

In general, the inventive arrangements relate to medical imaging systems, and more specifically, to combining medical imaging systems, such as, for example, providing an ultrasound docking port on a non-ultrasound medical imaging system.

2. Description of Related Art

For illustrative, exemplary, representative, and non-limiting purposes, preferred embodiments of the inventive arrangements will be described in terms of medical imaging systems. For example, common medical imaging systems include medical equipment for radiology, functional imaging, molecular imaging, vascular imaging, fluoroscopy, angiography, mammography, neurology, oncology, radio pharmacology, x-ray, nuclear medicine (NM), magnetic resonance imaging (MRI), positron emission tomography (PET), computed tomography (CT), ultrasound, and/or the like. However, the inventive arrangements are not limited in these regards.

Now then, in multi-modality medical imaging systems, various imaging techniques can be combined to acquire patient images. For example, in a PET/CT imaging system, imaging from both modalities can be combined to enhance patient imagery. While one such system can capture functional imagery, the other can capture anatomical imagery, with each enhancing and/or complementing the other. However, most medical imaging systems are not well-equipped to readily accommodate additional modality imaging systems, and successful fusion thereof remains desirable—e.g., progress has been made in image registration between modalities, but little less.

Thus, continued progress remains desirable for combining many attributes of multi-modality medical imaging systems. For example, it remains desirable to provide many medical imaging systems with a convenient ultrasound docking port, particularly as ultrasound equipment and/or systems become more portable, ubiquitous, useful, and/or practical, as a desirable add-in to numerous other imaging modality applications.

SUMMARY

In various embodiments, multi-modality medical imaging systems and methods combine and/or fuse ultrasound medical imaging systems and non-ultrasound medical imaging systems, particularly via a docking port carried on, and/or otherwise supported by, the non-ultrasound medical imaging system so as to receive the ultrasound medical imaging system. The ultrasound medical imaging system and non-ultrasound medical imaging system can communicate directly, indirectly, and/or wirelessly.

When they are joined, each system can be configured for cross-imaging in the other modality. Each system can also be configured to display medical imagery from the other modality on respective and/or combined displays. Each system can also be configured to be controlled by a user interface on the other system and/or a common user interface. Registry between patient imagery is provided, as is improved workflow between the systems.

BRIEF DESCRIPTION OF SEVERAL VIEWS OF THE DRAWINGS

A clear conception of the advantages and features constituting inventive arrangements, and of various construction and operational aspects of typical mechanisms provided by such arrangements, are readily apparent by referring to the following illustrative, exemplary, representative, and non-limiting figures, which form an integral part of this specification, in which like numerals generally designate the same elements in the several views, and in which.

DETAILED DESCRIPTION OF PREFERRED EMBODIMENTS

Referring now to the figures, preferred embodiments of the inventive arrangements will be described in terms of medical imaging systems. However, the inventive arrangements are not limited in this regard. For example, while variously described embodiments may provide ultrasound docking techniques in other imaging modality contexts, other applications are also hereby contemplated, including various other consumer, industrial, radiological, and inspection systems, and/or the like.

Figure 1:
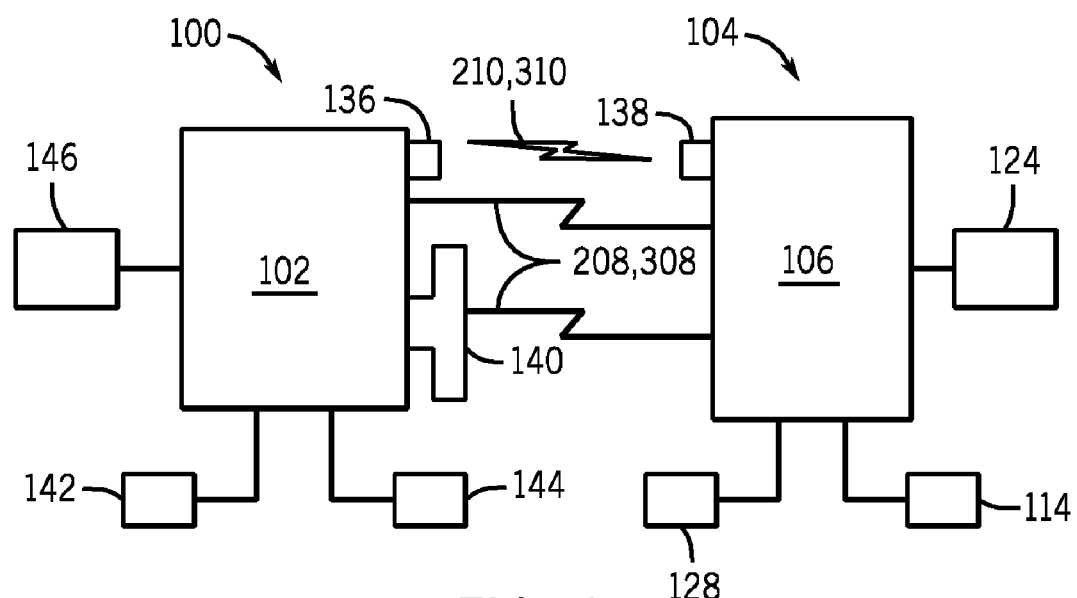
FIG. 1 illustrates a block diagram of a medical imaging system configured in accordance with various embodiments of the inventive arrangements.

Now then, referring to FIG. 1, a first medical imaging system 100 includes medical equipment 102 for an imaging modality, such radiology, functional imaging, molecular imaging, vascular imaging, fluoroscopy, angiography, mammography, neurology, oncology, radio pharmacology, x-ray, NM, MRI, PET, CT, and/or various combinations thereof, and this first medical imaging system 100 is not particularly configured for ultrasound imaging. In an x-ray based first medical imaging system 100, for example, an x-ray source (not shown) and detector (not shown) operate together to form patient images. In any event, a second medical imaging system 104 also includes medical equipment 106 for an imaging modality, and this second medical imaging system 104 is particularly configured for ultrasound imaging.

Figure 2:
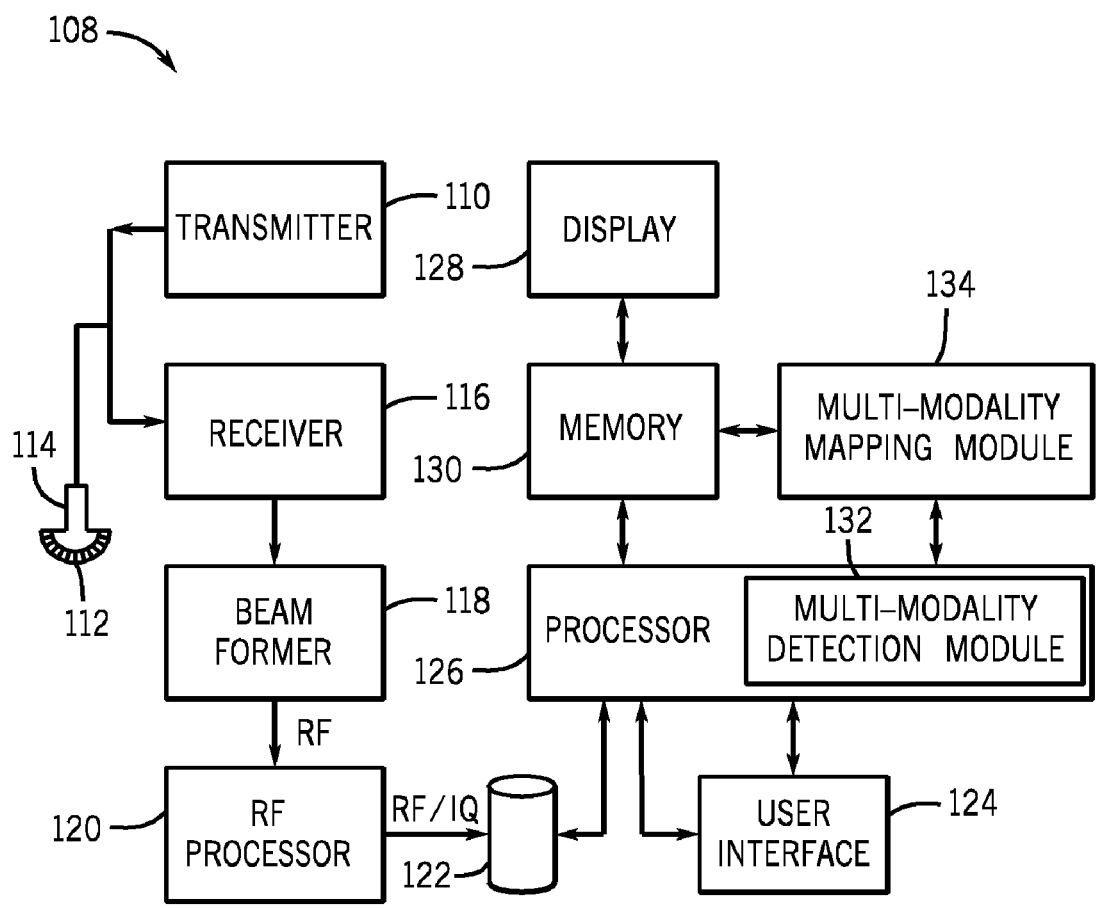
FIG. 2 illustrates a block diagram of an ultrasound system configured in accordance with various embodiments of the inventive arrangements.

Referring now to FIG. 2, taken in conjunction with FIG. 1, an ultrasound system 108 is depicted. More specifically, the ultrasound system 108 includes a transmitter 10 that drives transducers 112 within an ultrasound probe 114 to emit ultrasonic signals into an object, such as a body (not shown). A variety of geometries may be used. For example, in operation, the ultrasound system 108 may acquire data sets by various techniques (e.g., freehand scanning, scanning using transducers 112 having position sensors, scanning using a 2D or matrix array, 3D scanning, real-time 3D scanning, volume scanning, 4D scanning, etc.), particularly by moving the transducers 112 along a linear and/or arcuate path while scanning a region of interest, which may be moved manually, mechanically, electronically, and/or by any various combinations thereof.

In any event, the transmitted ultrasonic signals are backscattered from the object, such as from blood cells or muscular tissue within a body, to produce echo signals that return to the transducers 112. These echo signals are then received by a receiver 116 in communication with the transducers 112. These echo signals are then passed from the receiver 116 to a beamformer 118, which performs beamforming and outputs RF signal data therefrom. The RF signal data then passes from the beamformer 118 to an RF processor 120. In an optional embodiment, the RF processor 120 may also include a complex demodulator (not shown) that demodulates the RF signal data to form IQ data pairs that represent the echo signals. Either the RF signal data or IQ data pairs are then routed from the RF processor 120 to a RF/IQ buffer 122 for temporary storage. A user interface 124 can also be used to control operation of the ultrasound system 108, including, for example, controlling input of patient data, changing a scanning or display parameter, and/or the like.

Preferably, the ultrasound system 108 also includes a processor 126 to process the acquired ultrasound information (e.g., the RF signal data or IQ data pairs) from the RF/IQ buffer 122 and prepare frames of ultrasound information for display on a display 128. Preferably, the processor 126 is configured to perform one or more processing operations according to selectable functions performed on the acquired ultrasound information. For example, the acquired ultrasound information can be processed in real-time during a scanning session as the echo signals are received; additionally, and/or alternatively, the acquired ultrasound information can also be stored temporarily in the RF/IQ buffer 122 (or other) during a scanning session, and then processed in other than real-time in a live or off-line operation.

In a preferred embodiment, the ultrasound system 108 continuously acquires ultrasound information at a frame rate in excess of, for example, fifty frames per second, which is approximately the perception rate of the human eye. Thus, the acquired ultrasound information can be displayed on the display 128 at a slower frame-rate. Accordingly, a memory 130 can be provided between the processor 126 and the display 128 for storing processed frames of the acquired ultrasound information that are not yet ready and/or needed for immediate display on the display 128. In an exemplary embodiment, for example, the memory 130 is of sufficient capacity to store at least several seconds worth of processed frames of the acquired ultrasound information. Preferably, these frames of information are stored in a manner that facilitates their later retrieval according to an order and/or time and/or other of acquisition. In any event, the memory 130 may comprise any known data storage medium.

In addition, the processor 126 may also contain therewithin, and/or otherwise communicate with and/or control, a multi-modality detection module 132, which may be implemented in hardware, software, and/or any combination(s) thereof. More specifically, the multi-modality detection module 132 can be configured to receive signals from the user interface 124 through the processor 126, and it is particularly configured to recognize the presence and/or absence of the first medial imaging system 100. Alternatively, and/or additionally, the multi-modality detection module 132 may also be contained within and/or supported by the first medical imaging system 100 as well, in which it is configured to recognize the presence and/or absence of the second medial imaging system 104. It allows the medical imaging systems 100, 104 to recognize the presence and/or absence of one another.

Preferably, the multi-modality detection module 132 is configured to transfer information to a multi-modality mapping module 134, which is in communication with the memory 130 and/or remote therefrom. In any event, the multi-modality mapping module 134 may also be implemented in hardware, software, and/or any combination(s) thereof, and it may be implemented by the first medical imaging system 100 and/or second medical imaging system 104. It allows the medical imaging systems 100, 104 to map functions thereof based on received signals therefrom. The image detection and/or image mapping may change based on the state of the overall multi-modality medical imaging system—i.e., the first medical imaging system 100 and/or second medical imaging system 104.

Figure 3:
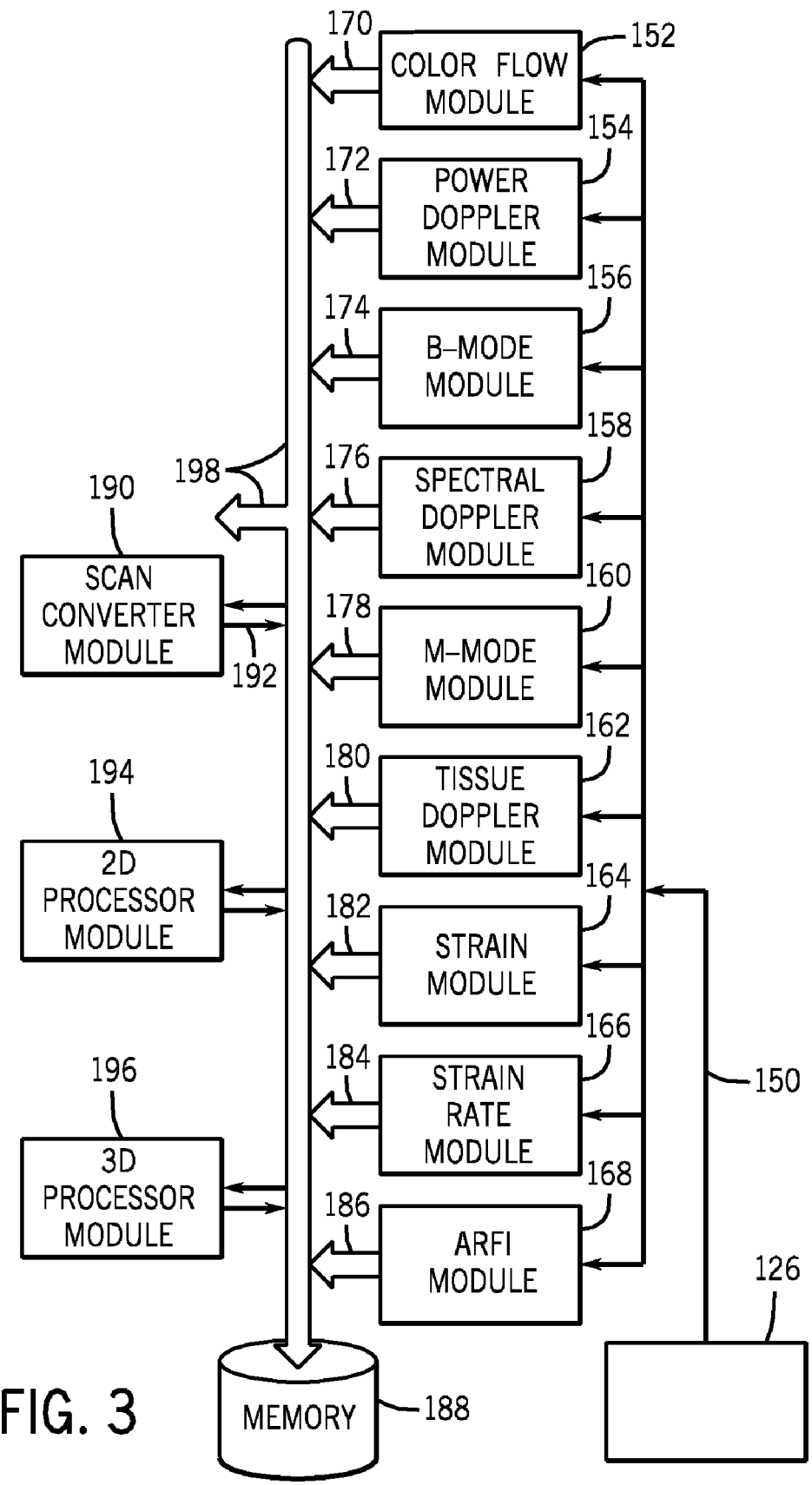
FIG. 3 illustrates representative sub-routine modules for operating the ultrasound system of FIG. 2.

Referring now to FIG. 3, an exemplary functional block diagram of the ultrasound system 108 of FIG. 2 is depicted. More specifically, the operation of the ultrasound system 108 is functionally illustrated as a conceptual collection of sub-module routines, although it may also be implemented in hardware, software, and/or any combination(s) thereof. For example, the sub-module routines of FIG. 3 may be implemented utilizing an off-the-shelf PC with i) a single processor, or ii) multiple processors with functional operations distributed between the processors, and/or otherwise. Alternatively, the sub-module routines may also be implemented utilizing a hybrid configuration, in which certain modular functions are implemented in hardware and other modular functions are implemented in software, etc.

In any event, operation of the sub-module routines is preferably controlled by the 126 processor and/or the like. More specifically, the sub-module routines 152-168 preferably perform mid-processor operations. For example, the processor 126 communicates ultrasound data 150 in one of several forms, such as IQ data pairs representing real and/or imaginary components associated with various data samples. The IQ data pairs can then be provided to one or more of a color flow module 152, power Doppler module 154, B-mode module 156, spectral Doppler module 158, and/or M-mode module 160. Optionally, other modules may also be included, such as a tissue Doppler module 162, strain module 164, strain rate module 166, and/or Acoustic Radiation Force Impulse (ARFI) module 168. The tissue Doppler module 162, strain module 164, and strain rate module 166 may, for example, together define an echocardiographic (ECG) processing configuration.

Preferably, each of the sub-module routines 152-168 are configured to process the IQ data pairs in a corresponding manner to respectively generate, for example, color-flow data 170, power Doppler data 172, B-mode data 174, spectral Doppler data 176, M-mode data 178, tissue Doppler data 180, strain data 182, strain rate data 184, and/or ARFI data 186, all of which may be stored in a memory 188, such as the memory 130 of FIG. 2, before subsequent processing. The data 170-186 may be stored, for example, as sets of vector data values, where each set defines an individual ultrasound image frame. The vector data values can be organized, for example, based on a polar coordinate system.

In addition, a scan converter module 190 can access vector data values associated with an image frame and convert the vector data values into Cartesian coordinates to generate an ultrasound image frame 192, particular formatted for display on the display 128 (see FIG. 2). The ultrasound image frames 192 generated by the scan converter module 190 can also be provided back to the memory 188 for subsequent processing, such as by a 2D processor module 194 and/or a 3D processor module 196, and/or the like, and they may be communicated over a bus 198 to a database (not shown) and/or to other processors (not shown) for additional and/or subsequent processing.

Figure 4:
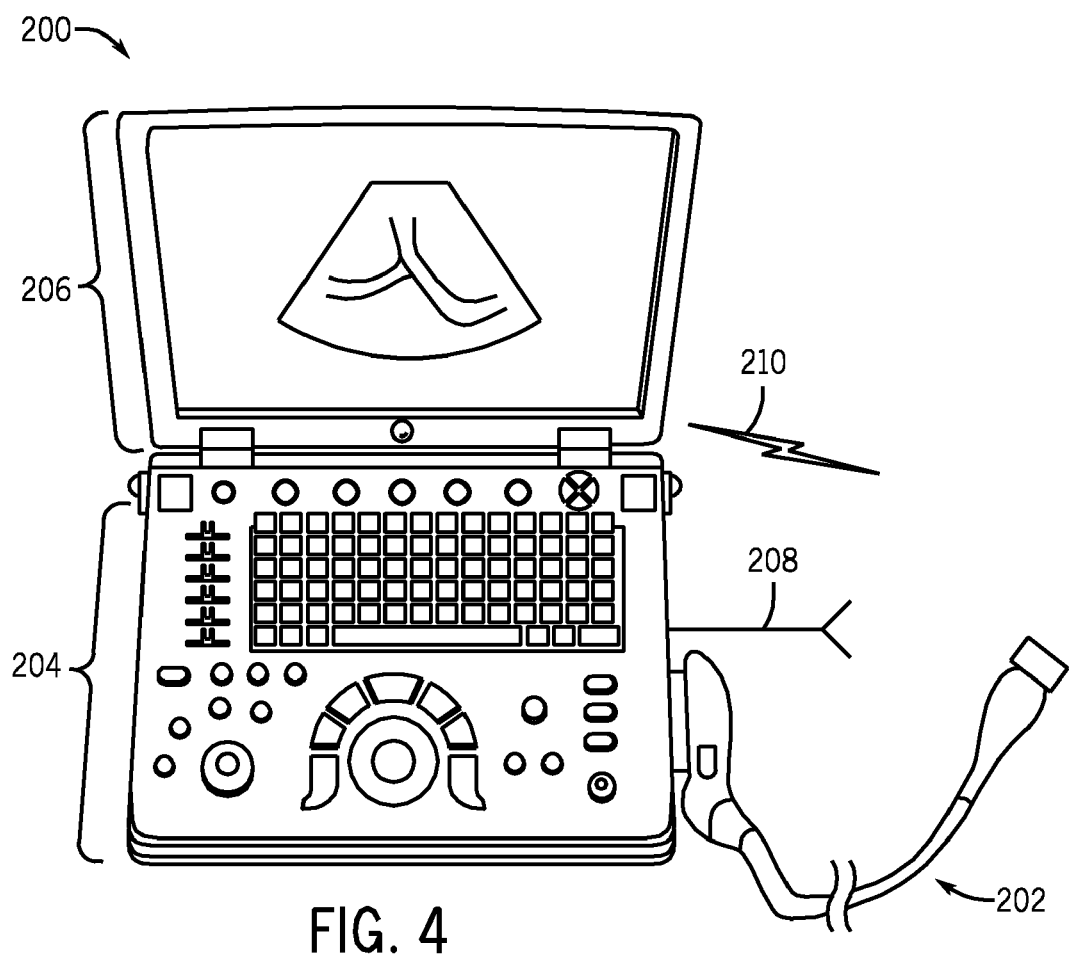
FIG. 4 illustrates an embodiment of a light-weight portable ultrasound system configured in accordance with various embodiments of the inventive arrangements.

Referring now to FIG. 4, an exemplary embodiment of a light-weight portable ultrasound system 200, configured in accordance with various embodiments of the inventive arrangements, is shown. More specifically, the ultrasound system 108 of FIG. 2 is configured as the light-weight portable ultrasound system 200, including a probe 202, user interface 204, and/or display 206. As depicted, the display 206 is an integrated component of the light-weight portable ultrasound system 200, although it may also be separate therefrom (not shown). Such a light-weight portable ultrasound system 200 is particularly well-suited to be carried under a person's arms, or in an approximately briefcase-sized carrying case, backpack, and/or the like. For example, it may be dimensioned similar to a laptop computer, and/or the like, such as being approximately 10 inches×14 inches and/or weighing approximately 10 pounds or less, such that it is easily portable by a user. In one embodiment, it communicates with other equipment, such as the first medical imaging system 100 (see FIG. 1), using a direct connection 208, such as a serial cable, parallel cable, USB port, and/or LAN line. In another embodiment, it communicates with other equipment, such as the first medical imaging system 100 (see FIG. 1), using an indirect and/or wireless connection 210.

Figure 5:
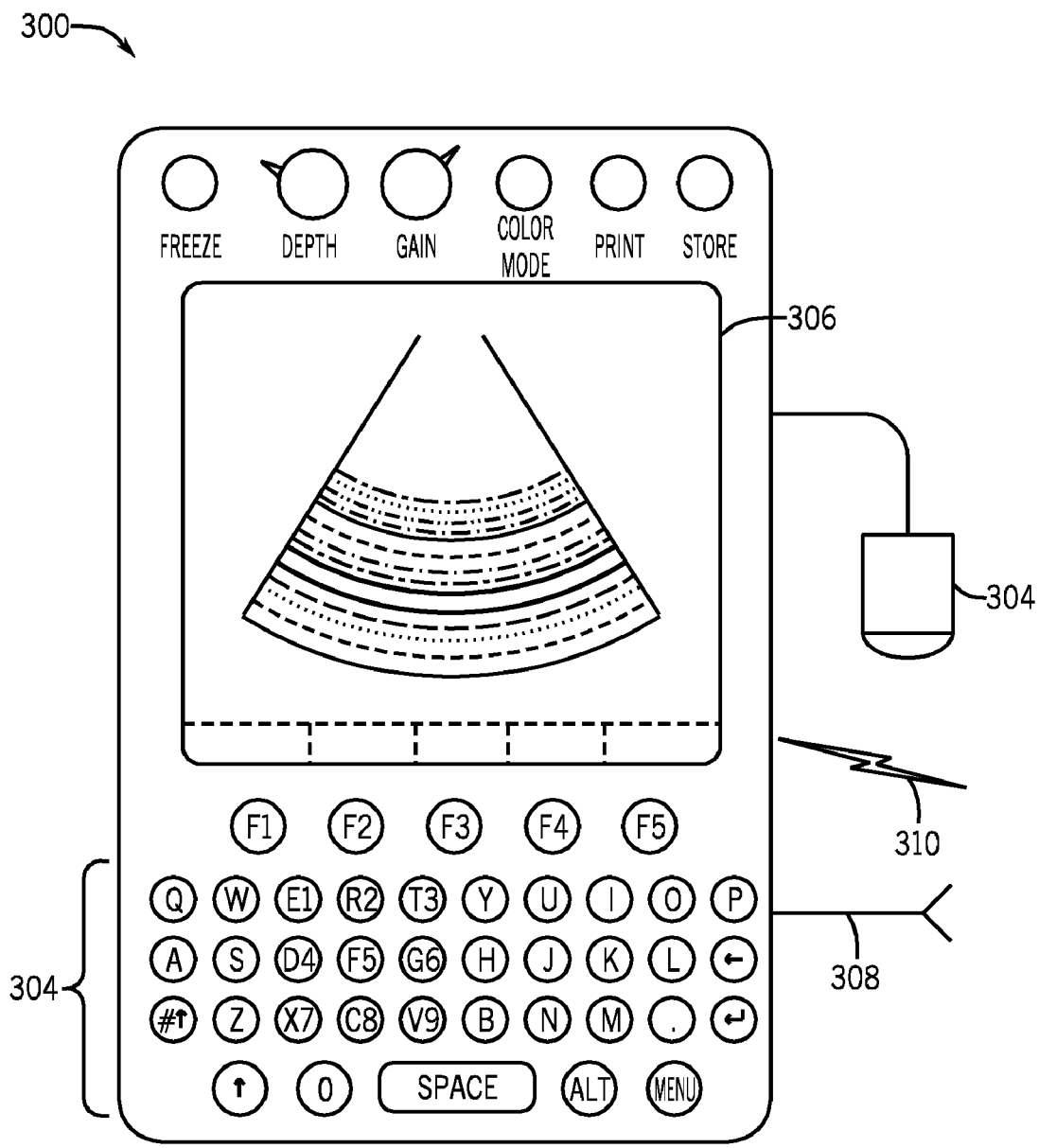
FIG. 5 illustrates an embodiment of an ultra light-weight portable ultrasound system configured in accordance with various embodiments of the inventive arrangements.

Referring now to FIG. 5, another exemplary embodiment of an ultra light-weight portable ultrasound system 300, configured in accordance with various embodiments of the inventive arrangements, is shown. More specifically, the ultrasound system 108 of FIG. 2 is configured as the ultra light-weight portable ultrasound system 300, including a probe (not shown), user interface 304, and/or display 306. As depicted, the display 306 is an integrated component of the ultra light-weight portable ultrasound system 300, although it may also be separate therefrom (not shown). Such an ultra light-weight portable ultrasound system 300 is particularly well-suited to be carried in a person's hands, or in a pocket, belt clip, purse, and/or the like. For example, it may be dimensioned similar to a stethoscope, cell phone, palm computer, personal digital assistant (PDA), portable media player, iPOD by Apple Inc. of Cupertino, Calif., and/or the like, such as being approximately 2 inches×4 inches and/or weighing approximately 1 pound or less, such that it is easily portable by a user. In one embodiment, it communicates with other equipment, such as the first medical imaging system 100 (see FIG. 1) using a direct connection 308, such as a serial cable, parallel cable, USB port, and/or LAN line. In another embodiment, it communicates with other equipment, such as the first medical imaging system 100 (see FIG. 1) using an indirect and/or wireless connection 310.

Referring now back to FIG. 1, the inventive arrangements can now be better illustrated and appreciated. More specifically, the first medical imaging system 100 (non-ultrasound) and second medical imaging system 104 (ultrasound) communicate with one another through a direct connection 208, 308 and/or indirect and/or wireless connection 210, 310. Accordingly, physical and/or electrical connections are made between the first medical imaging system 100 and second medical imaging system 104, which allow power and/or data signals and/or the like to be shared therebetween. Communications can be unidirectional and/or bidirectional, as well as employ multiple lines and/or channels, as needed and/or desired, and particularly configured, for example, to enhance throughput.

In an embodiment of direct communication, the first medical imaging system 100 is configured with a docking station 140 to physically receive the second medical imaging system 104, thereby enabling transmissions therebetween. For example, with one suitable physical arrangement, the first medical imaging system 100 contains a receiving receptacle, such as, e.g., the docking station 140, into which the second medical imaging system 104 is received. This particular arrangement allows securing and/or releasably securing the first medical imaging system 100 and second medical imaging system 104 together.

In an embodiment of indirect and/or wireless communication, the first medical imaging system 100 is configured with a first wireless transmitter and/or receiver 136, and the second medical imaging system 104 is likewise configured with a second wireless transmitter and/or receiver 138, thereby enabling transmissions therebetween.

As such, the first medical imaging system 100 can display medical imaging information therefrom on a display 142 in communication therewith, as can the second medical imaging system 104 display medical imaging information therefrom on its display 128 in communication therewith. As needed and/or desired, however, the first medical imaging system 100 can also display medical imaging information on the display 128 of the second medical imaging system 104, as can the second medical imaging system 104 also display medical imaging information on the display 142 of the first medical imaging system 100. These images can also be displayed thereon in any suitable fashion, and the displays 128, 142 can also form and/or be a part of a singular and/or plural common display arrangement. In addition, one medical imaging system 100, 104 can be used to determine a region of interest, for example, while the other medical imaging system 100, 104 images thereabout.

In addition, as the second medical imaging system 104 includes an ultrasound probe 114 to emit ultrasonic signals into an object such as a body (not shown), so can the first medical imaging system 100 also contain an ultrasound probe 144. Accordingly, the ultrasound probes 114, 144 can either be fixed and/or docked to either the first medical imaging system 100 and/or second medical imaging system 104. As such, ultrasound images can be gathered by either or both of the first medical imaging system 100 and/or second medical imaging system 104, which can again be suitably displayed on the displays 128, 142. Processing power and/or other functionality can also be similarly shared therebetween the medical imaging systems 100, 104.

As such, the first medical imaging system 100 can operate and perform as an ultrasound imaging system, particularly when in communication with the second medical imaging system 104. Of course, the second medical imaging system 104 can also operate and perform as an ultrasound imaging system, including when in communication in with the first medical imaging system 100. Accordingly, the first medical imaging system 100 and second medical imaging system 104 are brought together and/or fused, both operationally and/or functionally.

In addition, when the first medical imaging system 100 operates in its traditional non-ultrasound imaging mode and the second medical imaging system 104 operates in its traditional ultrasound imaging mode, imagery therefrom can also be fused, including registering the imagery therebetween. In this context, registering imagery refers, for example, to bringing the geometries and/or coordinate systems of the imaged object together in a defined relationship, as between the first medical imaging system 100 and/or second medical imaging system 104. Accordingly, ultrasound data can be merged with before or after acquired images from other imaging modalities, such as the first medical imaging system 100, including both in real-time and/or delayed imagery. As such, imaging and/or other comparisons can be made while taking advantage of the respective strengths of each imaging modality. These comparisons can be either side-by-side on one or the other or both of the displays 128, 142, and/or by overlaying the images from the first medical imaging system 100 and/or second medical imaging system 104. It can also be done in real-time and/or sometime afterwards.

In addition, as the second medical imaging system 104 includes a user interface 124 to interface therewith, the first medical imaging system 100 also includes a user interface 146 to interface therewith. In addition, the first medical imaging system 100 can be controlled by the user interface 124 of the second medical imaging system 104, while the second medical imaging system 104 can also be controlled by the user interface 146 of the first medical imaging system 100. In addition, the user interfaces 124, 146 can also form and/or be a part of a singular and/or plural user interface. When the medical imaging systems 100, 104 are connected, one of the user interfaces 124, 146 and/or displays 128, 142 can also control and/or dominate the other respective user interface 124, 146 and/or displays 128, 142.

It can be noted, for example, that while providing and/or operating a separate first medical imaging system 100 and/or separate second medical imaging system 104 will ordinarily require multiple operators (not shown) and/or a single operator (not shown) to separately control each system 100, 104 individually, this can result in, for example, medical errors due to incorrect or improper data input, delays when moving patients (not shown) between systems 100, 104, etc. However, with the inventive arrangements, on the other hand, these problems can be minimized and/or overcome. Exam time can be decreased, yet improved medical care is provided. A single work flow (and/or single work list for a single patient) is thereby provided across a multi-modality platform.

Since the first medical imaging system 100 and second medical imaging system 104 are in communication with one another through the direct connection 208, 308 and/or indirect and/or wireless connection 210, 310, each system 100, 104 preferably detects the other system 100, 104 when they are working and/or functioning in tandem. For example, a manual operation on either the first medical imaging system 100 and/or second medical imaging system 104 could be used to determine the presence of the other system 100, 104, as well as could a periodic polling configuration, as needed and/or desired, as well as via the direct connection 208, 308 through the docking station 140 and/or the like. Accordingly, the multi-modality detection module 132 and/or multi-modality mapping module 134 (see FIG. 2) can be suitably invoked.

Automatic protocol configurations can also be generated based on system configurations, including, for example, the number, type, etc. of ultrasound probes 114, 144 each system 100, 104 is using. In addition, automatic synchronization of patient data and/or images from the first medical imaging system 100 and/or second medical imaging system 104 can also be provided, and multi-modality images can be gathered in a single patient examination from a single, combined imaging platform.

In accordance with all of the foregoing, technical effects include providing medical imaging systems and methods containing dedicated ultrasound docking ports. More specifically, ultrasound medical imaging systems and non-ultrasound medical imaging systems are combined and/or configured for communicating with one another via a docking port provided on, and/or otherwise supported by, the non-ultrasound medical imaging system, which is particularly outfitted and/or configured to receive the ultrasound medical imaging system. Medical patient workflows and/or imagery, in particular, are thereby enhanced.

Accordingly, it should be readily apparent that this specification describes illustrative, exemplary, representative, and non-limiting embodiments of the inventive arrangements. Accordingly, the scope of the inventive arrangements are not limited to any of these embodiments. Rather, various details and features of the embodiments were disclosed as required. Thus, many changes and modifications—as readily apparent to those skilled in these arts—are within the scope of the inventive arrangements without departing from the spirit hereof, and the inventive arrangements are inclusive thereof. Accordingly, to apprise the public of the scope and spirit of the inventive arrangements, the following claims are made:

What is claimed is:

1. A multi-modality medical imaging system, comprising:
   an ultrasound medical imaging system configured for ultrasound imaging; and
   a non-ultrasound medical imaging system configured for non-ultrasound imaging,
   wherein the ultrasound medical imaging system and non-ultrasound medical imaging system are configured for communication with one another through a docking port supported by the non-ultrasound medical imaging system and configured to physically receive the ultrasound medical imaging system to releasably secure the ultrasound medical imaging system and the non-ultrasound medical imaging system together.

2. The medical imaging system of claim 1, wherein the ultrasound medical imaging system and non-ultrasound medical imaging system are configured to communicate directly.

3. The medical imaging system of claim 1, wherein the ultrasound medical imaging system and non-ultrasound medical imaging system are configured to communicate indirectly.

4. The medical imaging system of claim 1, wherein the ultrasound medical imaging system and non-ultrasound medical imaging system are configured to communicate wirelessly.

5. The medical imaging system of claim 1, wherein the non-ultrasound medical imaging system is configured for controlling ultrasound medical imaging using the ultrasound medical imaging system when in communication with the ultrasound medical imaging system.

6. The medical imaging system of claim 1, wherein the ultrasound medical imaging system is configured for controlling non-ultrasound medical imaging using the non-ultrasound medical imaging system when in communication with the non-ultrasound medical imaging system.

7. The medical imaging system of claim 1, wherein the ultrasound medical imaging system is portable and the docking port is configured as a receiving receptacle into which the ultrasound medical imaging system is received and releasably secured.

8. The medical imaging system of claim 1, wherein the non-ultrasound medical imaging system includes an ultrasound probe.

9. The medical imaging system of claim 1, wherein the ultrasound medical imaging system is configured for ultrasound medical imaging using a probe of the non-ultrasound medical imaging system.

10. The medical imaging system of claim 1, wherein the non-ultrasound medical imaging system is configured for controlling ultrasound medical imaging using the ultrasound medical imaging system and a probe of the ultrasound medical imaging system.

11. The medical imaging system of claim 1, wherein the ultrasound medical imaging system is configured to display images on a display of the non-ultrasound medical imaging system.

12. The medical imaging system of claim 1, wherein the non-ultrasound medical imaging system is configured to display images on a display of the ultrasound medical imaging system.

13. The medical imaging system of claim 1, wherein the ultrasound medical imaging system is configured to display images on a display of the non-ultrasound medical imaging system and the non-ultrasound medical imaging system is configured to display images on a display of the ultrasound medical imaging system.

14. The medical imaging system of claim 1, wherein the ultrasound medical imaging system and non-ultrasound medical imaging system are configured to share a common display.

15. The medical imaging system of claim 1, wherein imagery between the ultrasound medical imaging system and non-ultrasound medical imaging system is registered.

16. The medical imaging system of claim 1, wherein the ultrasound medical imaging system is configured to be controlled by a user interface of the non-ultrasound medical imaging system.

17. The medical imaging system of claim 1, wherein the non-ultrasound medical imaging system is configured to be controlled by a user interface of the ultrasound medical imaging system.

18. The medical imaging system of claim 1, wherein the ultrasound medical imaging system and non-ultrasound medical imaging system are configured to be controlled by a common user interface.

19. The medical imaging system of claim 1, wherein the ultrasound medical imaging system and non-ultrasound medical imaging system are configured to be controlled by a common user interface and share a common display.

20. A multi-modality medical imaging method, comprising:
providing an ultrasound medical imaging system configured for ultrasound imaging;
providing a non-ultrasound medical imaging system configured for non-ultrasound imaging and in communication with the ultrasound medical imaging system; and
joining the ultrasound medical imaging system and the non-ultrasound medical imaging system through a docking port supported by the non-ultrasound medical imaging system and configured to physically receive the ultrasound medical imaging system to releasably secure the ultrasound medical imaging system and the non-ultrasound medical imaging system together.

* * * * *